United States Patent [19]
Garman

[11] Patent Number: 5,975,900
[45] Date of Patent: Nov. 2, 1999

[54] ROTATABLE MEDICAL AND/OR DENTAL INSTRUMENT HAVING A VARIABLE SPEED TRANSMISSION

[75] Inventor: Gary T. Garman, La Verne, Calif.

[73] Assignee: Ormco Corporation, Glendora, Calif.

[21] Appl. No.: 09/144,700

[22] Filed: Sep. 1, 1998

[51] Int. Cl.[6] .................................................. A61C 1/08
[52] U.S. Cl. .......................................... 433/105; 433/126
[58] Field of Search ..................... 433/105, 130, 433/126, 133, 146; 408/133; 74/416, 417, 332

[56] References Cited

U.S. PATENT DOCUMENTS

| | | | |
|---|---|---|---|
| 3,229,369 | 1/1966 | Hoffmeister et al. | 433/105 |
| 3,436,980 | 4/1969 | Loge et al. | 433/105 |
| 4,278,428 | 7/1981 | Straihammer et al. | 433/105 |
| 4,306,865 | 12/1981 | Leonard | 433/105 |
| 5,281,138 | 1/1994 | Rosensstatter | 433/105 |
| 5,569,034 | 10/1996 | Meller et al. | 433/105 |

*Primary Examiner*—Gene Mancene
*Assistant Examiner*—Pedro Philogene
*Attorney, Agent, or Firm*—Wood, Herron & Evans, L.L.P.

[57] ABSTRACT

A handheld medical instrument for rotating a tool including a support structure having a portion that may be gripped by a user, and an electric motor having an output rotatable at a first speed. A tool rotating shaft extends from the support structure and is adapted to be coupled to a tool to rotate the tool at a second speed. A variable speed transmission is operatively coupled between the output of the electric motor and the tool rotating shaft to transfer rotation therebetween and is selectively adjustable between at least two different ratios of the first speed relative to the second speed.

33 Claims, 3 Drawing Sheets

ROTATABLE MEDICAL AND/OR DENTAL INSTRUMENT HAVING A VARIABLE SPEED TRANSMISSION

FIELD OF THE INVENTION

The present invention generally relates to rotatable medical and dental instruments for variable speed rotation of tools, such as rotatable files, drills or shaping tools. More specifically, the invention relates to handheld instruments in which it is desirable to rotate a medical or dental tool at a relatively wide variety of speeds.

BACKGROUND OF THE INVENTION

Electrically operated, handheld devices are commonly used today in various medical and dental procedures. These devices may be used, for example, to rotate burrs, drills, and dental files for cutting away or shaping different types of tissue. Typically, these devices include an electronic controller, a variable speed handheld motor, and a gear head. The controller is electrically connected to the motor and can vary the power to the motor thus varying the motor output speed. The gear head includes an output which is connected to the desired tool for rotating the tool at a predetermined speed. Gear heads are generally available in many different input/output speed ratios and a selected gear head is typically connected to the motor both to provide a mechanical connection to the desired tool and to step-up or step-down the rotational speed of the tool relative to the speed of the motor.

A significant problem with existing handheld instruments of this type is that the motors are usually limited to a small range of output speeds. A typical output speed of handheld instruments is approximately 1,000 rpm to 20,000 rpm. Tool rotation requirements, however, can often vary between 250 rpm and 200,000 rpm depending on the medical or dental procedure. For example, root canal files need to be rotated at relatively slow speeds of between about 250 rpm and about 500 rpm. Dental drills may be rotated in a range of about 2,000 rpm to about 4,000 rpm. Diamond burrs, for example, used for cleaning, shaping or polishing work in the dental field ideally rotate at relatively high speeds. These speeds may reach 150,000 rpm to 200,000 rpm or above. To achieve a wide range of different speeds, given the relatively limited speed range of a motor, different gear heads are purchased by end users to step-up (i.e., multiply) or step-down (i.e., reduce) the final output speed of the instrument or tool according to the needs of the user. This typically requires the purchase of a number of different, and expensive, gear heads. In addition, the output speed displayed on the motor controller typically relates only to the motor output and thus the actual final tool speed must be separately calculated by the user depending upon the specific gear ratio of the chosen gear head. These calculations can be error-prone.

In view of these and other problems in the art, it would be desirable to provide a medical and/or dental instrument for rotating a tool that can reduce or eliminate the need for several different gear heads to perform a number of different medical or dental procedures.

SUMMARY OF THE INVENTION

The present invention therefore provides a handheld medical and/or dental instrument for rotating a tool, which generally includes a support structure preferably having a housing that may be gripped by a user and an electric motor having an output rotatable at a first speed. A tool rotating shaft, which may be rigid or flexible, extends from the support structure and is adapted to be coupled to a tool and rotated at a second speed. In accordance with the invention, a variable speed transmission is operatively connected between the output of the electric motor and the tool rotating shaft to transfer rotation therebetween. The transmission includes a gear system which is selectively adjustable between at least two different ratios of the first speed relative to the second speed.

The present invention more specifically provides a transition gear mounted for operation between an input gear and an output gear. The transition gear is movable between at least two positions by an actuating member to facilitate a step-up and/or step-down in the rotational speed of the output gear as compared to the rotational speed of the input gear. Generally stated, therefore, a user holding the medical or dental instrument may move the actuating member between the two positions to change the speed of the tool rotating shaft driven by the output gear of the transmission. The input, output and transition gears are preferably constructed as an instrument integrated with a handheld drive motor. Optionally, the motor may be located remote from the gear system or variable transmission of this invention. As still another option, the gear system or variable transmission may be made part of a gear head which is selectively attachable to the handheld instrument. In any of the possible forms, the invention can reduce or eliminate the need for multiple, separate gear heads.

Preferably, the transition gear is part of a planetary gear system with at least a portion of the planetary gear system being movable between two positions. In the preferred embodiment more specifically disclosed herein, the planetary gear system includes an internally toothed annulus gear which is fixed within the support structure or housing and a plurality of planet gears which are selectively engageable with the annulus gear, but also disengageable therewith to facilitate either a step-up or step-down in the input/output speed ratio of the instrument. For example, the planet gears may be moved by the actuating member between three positions with a first position facilitating a step-down or reduction in the output speed relative to the input speed, a second position facilitating a 1:1 ratio or direct drive between the input speed and output speed, and a third position facilitating a step-up or multiplication in the output speed relative to the input speed.

As mentioned above, the support structure may be a housing which at least holds the gears necessary for the variable speed transmission and which may also contain an electric motor coupled to the input gear. The actuating member may be a manually actuable knob or switch connected to the planet gears and mounted for axial movement generally along an outside surface of the housing. The electric motor may more specifically be a variable speed motor so that the tool may be rotated in a selected speed range determined both by the speed range of the motor and the selected gear ratio determined by position of the manual actuating member. A position indicating device, such as a three position electric switch, may be coupled to the actuating member and electrically connected to a control for indicating the position of the actuating member. The control may then operate to calculate and display the correct speed of the tool based on the speed of the motor multiplied by the selected gear ratio of the gear head.

In one alternative embodiment, the input gear may be operatively connected with a flexible drive member extending from the housing and coupled with an electric motor.

This alternative can, for example, facilitate the use of a larger, high torque electric motor in place of a motor incorporated into or attached to the handheld housing. Such larger motors may be desirable in certain applications that require higher torque, especially when larger step-up ratios are used which result in corresponding reductions in output torque. In these cases, the higher torque motor can still supply sufficient output torque at the tool despite the torque reduction due to the speed multiplying effect of the transmission.

These and other objectives and advantages of the invention will become more readily apparent to those of ordinary skill in the art upon review the following detailed description of the preferred embodiments, taken in conjunction with the drawings.

DETAILED DESCRIPTION OF THE PREFERRED EMBODIMENTS

Figure 1:
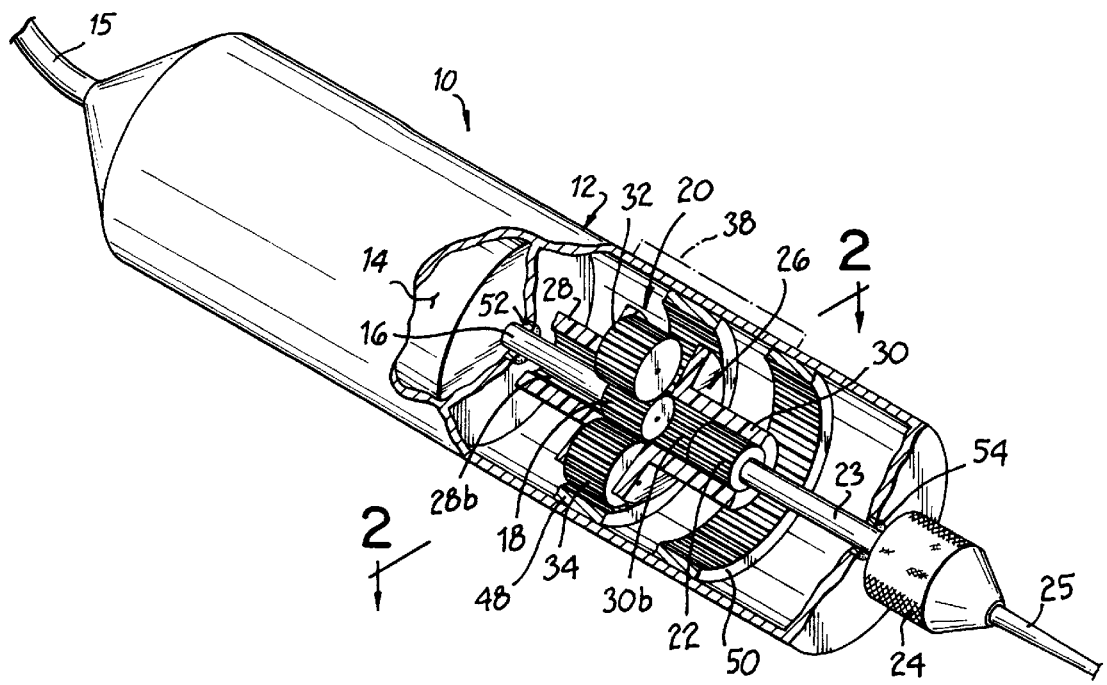
FIG. 1 is a partially fragmented perspective view of a medical or dental instrument constructed in accordance with one preferred embodiment of the invention.

Although the present invention may take on many forms, one preferred embodiment of a handheld medical or dental instrument 10 is shown in FIG. 1. Instrument 10 generally includes a housing 12 which may incorporate an electric motor 14 therein receiving electrical current from a power cord 15. Power cord 15 may be connected with a motor control, as will be discussed below. Motor 14 includes an output shaft 16 connected with an input gear 18 of a gear system 20 constructed in accordance with the invention. Motor 14 may be a conventional variable speed AC or DC motor which provides some range of variation in the rotational speed of output shaft 16. As will be discussed herein, gear system 20 conveniently provides further speed variation to instrument 10.

Figure 2:
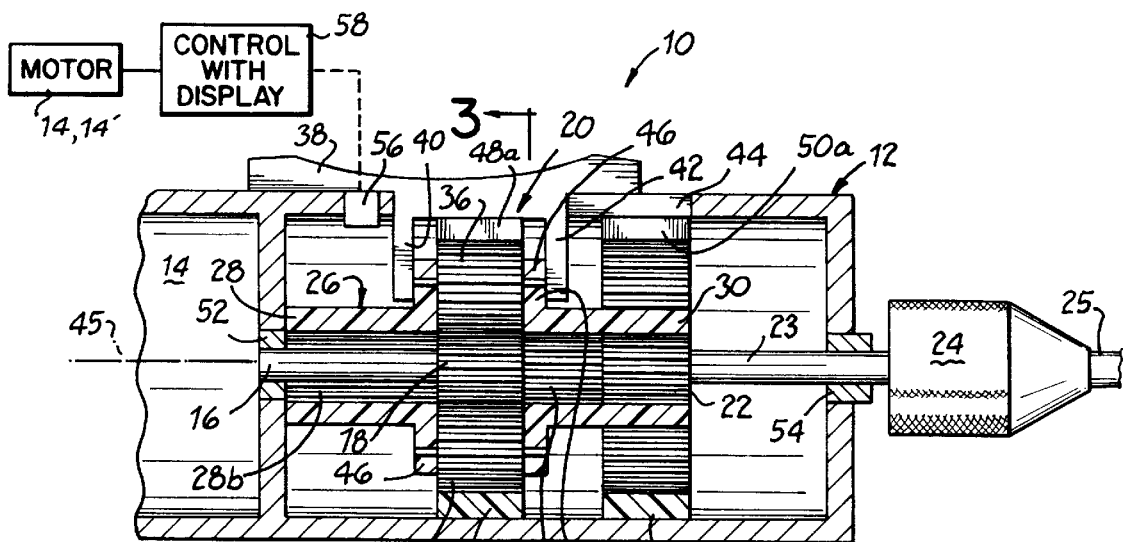
FIG. 2 is a cross sectional view generally taken in the direction of line 2—2 of FIG. 1 and showing the gear system in a first step-down or speed reducing mode.

As further shown in FIGS. 1 and 2, gear system 20 includes an output gear 22 connected with an output shaft 23 which may be operatively connected to rotate a tool holder 24 mounting a tool 25, such as a dental file. An internally toothed carrier 26 is connected generally between input gear 18 and output gear 22. Specifically, carrier 26 includes a first internally splined or toothed member 28 and a second internally splined or toothed member 30 which are adapted to respectively receive input and output gears 18, 22. In the preferred embodiment, a plurality of planet gears 32, 34, 36 are connected for rotation with respect to carrier 26. Planet gears 32, 34, 36 also rotate with carrier 26 as will be explained in more detail below. An actuating member 38, which may be in the form of a finger switch, is connected with carrier 26 as best shown in FIG. 2. Actuating member 38 includes a pair of arms 40, 42 respectively engaged with toothed carrier members 28, 30.

Figure 2B:
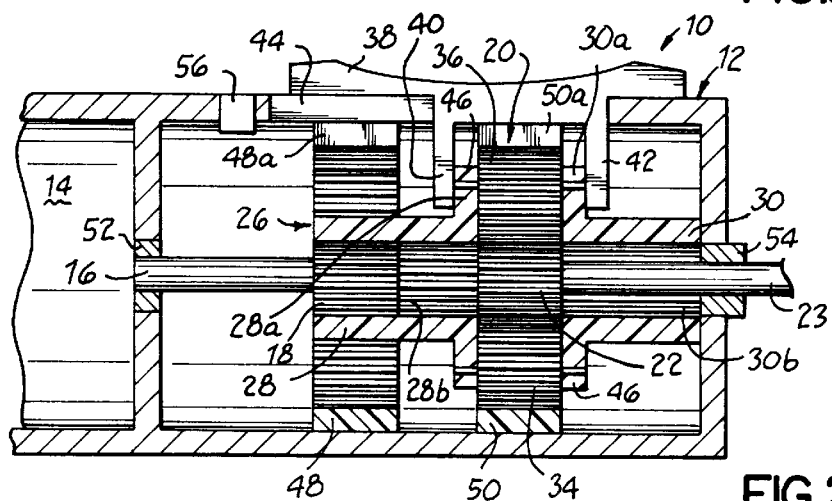
FIG. 2B is a view similar to FIGS. 2 and 2A, but showing the gear system in a third step-up or speed multiplying mode.
Figure 3:
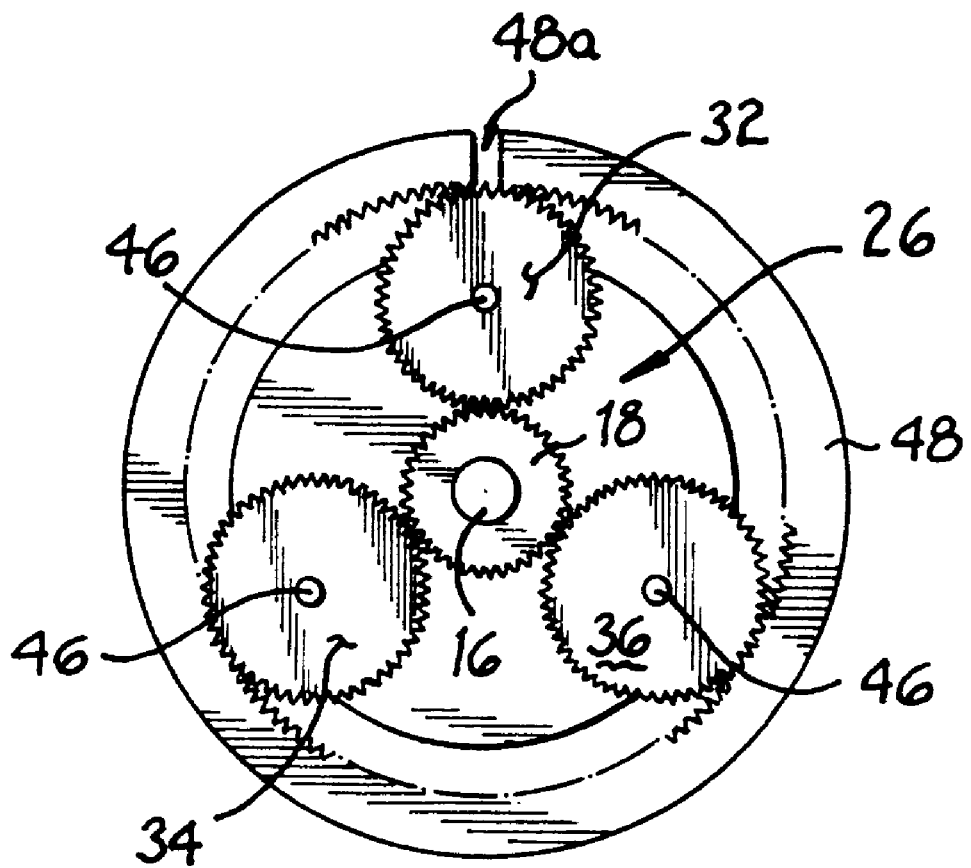
FIG. 3 is a cross sectional view taken generally along line 3—3 of FIG. 2 but eliminating the housing and actuating member for clarity.

As further shown in FIG. 2, arms 40, 42 preferably extend through a slot 44 in housing 12 for sliding movement parallel to axis 45 of instrument 10. For example, arms 40, 42 may be received on opposite sides of circumferential flange portions 28a, 30a of toothed carrier members 28, 30. In this manner, toothed carrier members 28, 30 may be moved in axial, opposite directions by actuating member 38. As further shown best in FIGS. 2 and 3, pins 46 may be used to secure planet gears 32, 34, 36 to carrier flange portions 28a, 30a for rotation with respect thereto. Additionally, a pair of internally toothed annulus gears 48, 50 are rigidly secured in a stationary manner within housing 12. Annulus gears 48, 50 are adapted to be selectively engaged in meshing relation with planet gears 32, 34, 36. Preferably, annulus gears 48, 50 each include axial slots 48a, 50a as shown in FIGS. 2–2B and 3 for allowing axial movement of arms 40, 42 therethrough while making speed range adjustments. As also shown in FIGS. 2–2B, suitable bearings or journals 52, 54 may be used to mount shafts 16 and 23 to housing 12. Also, a position indicating device, such as a conventional three position electric switch 56, may be used to indicate the position of actuating member 38, and therefore indicate to a control 58 which speed range has been selected by a user. As will be understood, the control can then make the simple calculation of multiplying the motor output speed by the selected gear ratio to accurately determine the rotational speed of tool 25.

Figure 1A:
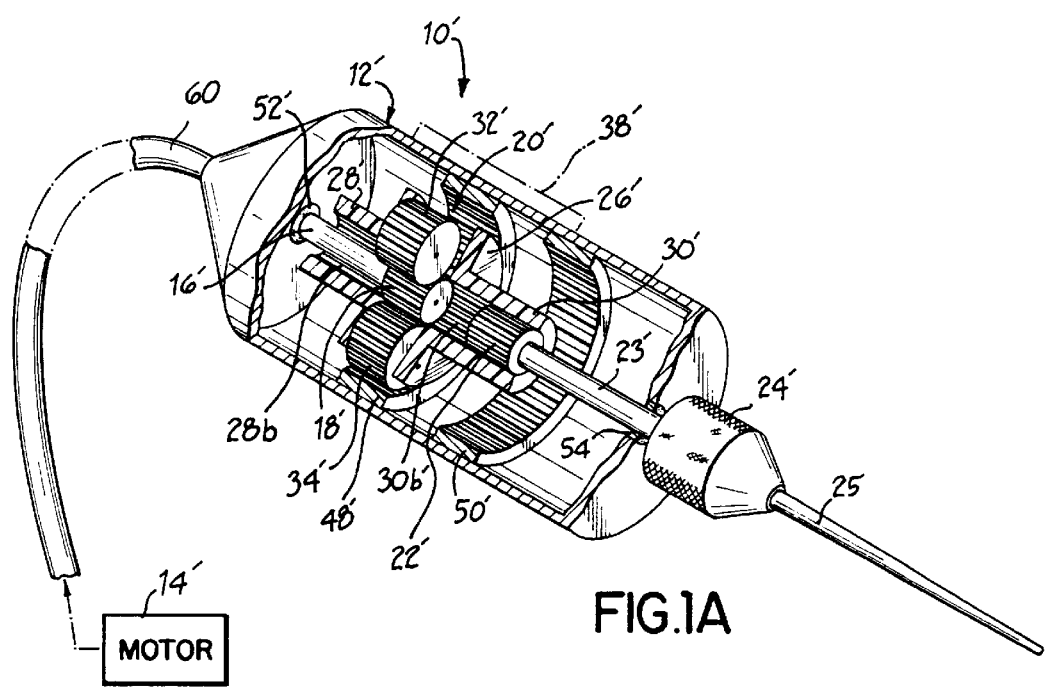
FIG. 1A is a partially fragmented perspective view, similar to FIG. 1, but showing an alternative embodiment of the present invention.

Referring briefly to FIG. 1A, an alternative embodiment of a medical instrument 10' constructed in accordance with the invention is shown and essentially utilizes a remotely connected electric motor 14'. Motor 14' is connected by a flexible drive cable 60 to shaft 16' which may be connected to an input gear 18' forming part of the same type of gear system 20' as described above with respect to the remaining figures. It will be appreciated that like numerals in FIG. 1A with prime marks (') represent like structure with the first embodiment and additional description thereof is not required. One of the main purposes of the embodiment shown in FIG. 1A is to provide more versatility in the selection of motor 14'. For example, a larger motor, which can exert higher torque than motor 14, may be selected for the remotely situated motor 14'. This would allow the transfer of a higher amount of torque to tool 25 in those situations requiring such torque. Also, the design in FIG. 1A makes the handheld piece, as generally defined by housing 12', smaller and more easily manipulated by the user. It will further be appreciated that a handheld instrument constructed in accordance with the invention may also more remotely locate gear system 20 and attach a suitable flexible drive cable (not shown) generally between the inventive gear system or transmission and an output shaft, such as shaft 23. This would make the handheld portion of the instrument even smaller and more lightweight.

The operation of instrument 10 will not be described with reference to the first embodiment, with the understanding that the description equally applies to the alternative embodiment of FIG. 1A, and more generally in principle to any other alternative embodiments falling within the spirit and scope of the invention. Referring specifically to FIG. 2, actuating member 38 and the connected carrier 26 and planet gears 32, 34, 36 are shown in one position which produces a step-down or reduction in the rotational speed of output shaft 23 as compared to the output shaft 16 of motor 14. It will be appreciated that the rotational speed of shaft 23 will be the same as the speed of output gear 22 and the rotational speed of shaft 16 will be the same as the speed of input gear 18. It will further be appreciated that additional gearing may be incorporated generally between tool 25 and output shaft 23 and/or between motor 14 and shaft 16, while still retaining the benefits of the invention as described herein. In the position shown in FIG. 2, as input gear 18 is rotated, planet gears 32, 34, 36 will be rotated about their respective axes and about the internally toothed surface of annulus gear 48 while also rotating the attached carrier 26. Due to the interaction of planet gears 32, 34, 36 with input gear 18, the rotational speed of carrier 26 will be slower than the rotational speed of input gear 18. Further, as the internally toothed carrier member 30 is engaged with output gear 22 in this position, carrier member 30 rotates output gear 22 at the reduced or step-down speed.

Figure 2A:
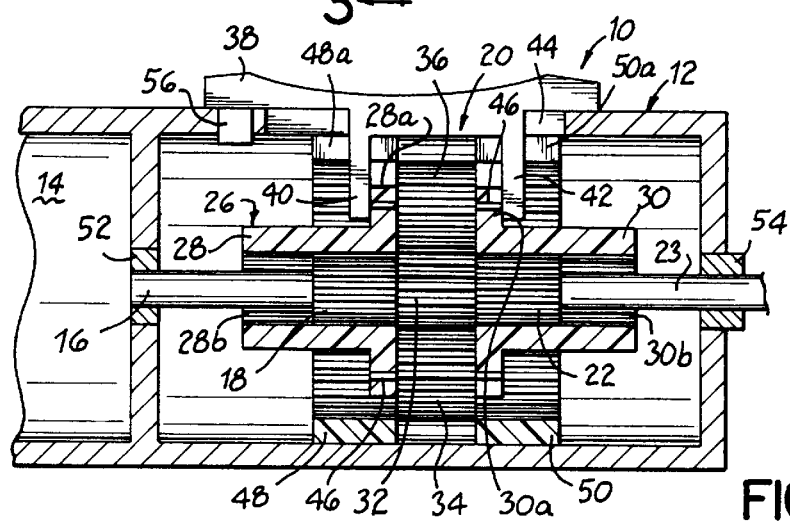
FIG. 2A is a view similar to FIG. 2 but showing the gear system in a second mode, producing a 1:1 ratio in input speed versus output speed.

In the position shown in FIG. 2A, actuating member 38 has been moved to an intermediate position generally located between input gear 18 and output gear 22. In this position, planet gears 32, 34, 36 are also located in a position between annulus gears 48, 50 so as to be disengaged therefrom. As further shown in FIG. 2A, input gear 18 is in meshing engagement with internally toothed carrier member 28, while output gear 22 is in meshing engagement with internally toothed carrier member 30. Therefore, in this position the rotation of input gear 18 will be transferred directly to output gear 22 through carrier 26 such that input and output gears 18, 22 rotate with the same speed. In this way, there is a 1:1 ratio between the output speed of motor 14 and the rotational speed of tool 25.

In FIG. 2B, actuating member 38 has been moved to another position in which planet gears 32, 34, 36 are aligned in meshing engagement with both internally toothed annulus gear 50 and output gear 22. Further, input gear 18 is still in meshing engagement with internally toothed carrier member 28. Thus, in the position shown in FIG. 2B, there will be a step-up or multiplication in the speed of shaft 23 with respect to shaft 16 of motor 14. This is because planet gears 32, 34, 36 will be rotated by input gear 18 through carrier 26. For each turn of input gear 18, planet gears 32, 34, 36 will turn output gear 22 multiple times or, in other words, will turn output gear 22 at a faster rate than input gear 18. In this manner, the speed of shaft 23 and, therefore, tool 25 will be stepped up or multiplied by a specific amount as compared to the output speed of motor 14, depending on the chosen gear ratios.

It will be understood that the stepped-up or stepped-down gear ratios may be selected according to the needs of the user. As only one example, in the position shown in FIG. 2 the chosen gearing may supply a 10:1 reduction in the speed of tool 25 as compared to the output speed of motor 14. Likewise, the gearing chosen for FIG. 2B may supply a 1:10 step-up or multiplication in the speed of tool 25 as compared to the output speed of motor 14. More specifically, input and output gears 18, 22 may have a 0.100 pitch diameter with ten teeth, planetary gears 32, 34, 36 may have a 0.400 pitch diameter with forty teeth and annulus gears 48, 50 may have a 0.900 pitch diameter with ninety teeth. Assuming a standard motor drive with a variable motor speed of 1,000–20,000 rpm, these gear sizes would provide output speed ranges of 100–2,000 rpm in a low range, 1,000–20,000 rpm in a 1:1 or direct drive gear ratio and 10,000–200,000 rpm in a high range.

The three position electric switch 56, schematically shown in FIGS. 2, 2A and 2B may be used to send a signal to control 58 indicative of the particular position of actuating member 38. Using the particular signal, control 58 can multiply the motor output speed by a factor determined by the gear ratio to obtain and display the rotational speed of tool 25 to the user. For example, in the example given above, when actuating member 38 is in the position shown in FIG. 2, a signal will be supplied to control 58 indicating that the control should multiply the motor output speed, which may be variable, by 1/10 to correctly indicate the final tool speed. In FIG. 2A, a multiplication factor of 1 would be prompted by device 56, and when actuating member 38 in the position shown in FIG. 2B, a multiplication factor of 10 would be prompted by device 56 within control 58. If other gearing is used, for example, between motor 14 and gear system 20 and/or between tool 25 and gear system 20, control 58 could, of course, be easily designed or programmed to take such gearing into account to calculate the correct tool speed.

While the present invention has been illustrated by a description of various embodiments and while these embodiments have been described in some detail, it is not the intention of the Applicant to restrict or in any way limit the scope of the appended claims to such detail. Additional advantages and modifications will readily appear to those skilled in the art. For example, many types of gear systems and transmissions may be used for carrying out the invention. Also, according to the needs of the user, shafts which are shown to be rigid shafts herein may be substituted with flexible shafts or drive cables. Additionally, although the terms medical instrument and dental instrument have been used herein, it should be understood that the term medical instrument generally references an instrument used in medical areas such as surgical, dental or orthodontic areas. The invention in its broader aspects is therefore not limited to the specific details, representative apparatus and method as shown and described. This has been a description of the present invention, along with the preferred methods of practicing the present invention as currently known. However, the invention itself should only be defined by the appended claims.

What is claimed is:

1. A handheld medical instrument for rotating a tool, the instrument comprising:

a support structure having a portion that may be gripped by a user;

an electric motor having an output rotatable at a first speed;

a tool rotating shaft extending from the support structure and adapted to be coupled to a tool and rotatable at a second variable speed; and a variable speed transmission operatively coupled between the output of the electric motor and the tool rotating shaft to transfer rotation therebetween, said transmission including a gear system which is selectively adjustable between at least two different ratios of the first speed relative to the second speed.

2. The instrument of claim 1, wherein the motor is mounted within the support structure.

3. The instrument of claim 1, wherein the gear system is adjustable between one ratio in which the first speed is less than the second speed and another ratio in which the first speed is equal to the second speed.

4. The instrument of claim 1, wherein the gear system is adjustable between one ratio in which the first speed is equal to the second speed and another ratio in which the first speed is greater than the second speed.

5. The instrument of claim 1, wherein the gear system is adjustable between one ratio in which the first speed is less than the second speed and another ratio in which the first speed is greater than the second speed.

6. The instrument of claim 1, wherein the gear system is adjustable between a first ratio in which the first speed is less than the second speed, a second ratio in which the first speed is equal to the second speed, and a third ratio in which the first speed is greater than the second speed.

7. A handheld medical instrument for rotating a tool, the instrument comprising:
a support structure;
an input gear mounted to the support structure for rotation by a drive at a first speed;
an output gear mounted to the support structure for rotation at a second variable speed and adapted to be coupled with the tool;
a transition gear mounted for operation between the input gear and the output gear, the transition gear being movable between at least two positions each position effecting a different ratio of the first speed relative to the second speed; and
a movable actuating member coupled with the transition gear for moving the transition gear between the two positions.

8. The instrument of claim 7, wherein the transition gear is part of a planetary gear system with at least a portion of the planetary gear system being movable between the two positions.

9. The instrument of claim 8, wherein at least a portion of the planetary gear system is movable by the actuating member between three positions with a first position facilitating a step-down in the second speed relative to the first speed, a second position facilitating a 1:1 ratio between the first speed and the second speed and a third position facilitating a step-up in the second speed relative to the first speed.

10. The instrument of claim 7, wherein the support structure is a housing containing the input and output gears and the transition gear.

11. The instrument of claim 10, wherein the actuating member is mounted for movement generally along an outside surface of the housing.

12. The instrument of claim 11 further comprising a handheld rotatable drive connected to rotate the input gear.

13. The instrument of claim 12, wherein the drive further comprises an electric motor.

14. The instrument of claim 13, wherein the electric motor is a variable speed motor.

15. The instrument of claim 7, wherein the input gear and output gear are each mounted within hollow, internally splined members and the transition gear is part of a planetary gear system mounted between the hollow, internally splined members.

16. The instrument of claim 7 further comprising a position indicating device coupled to the actuating member and electrically connected to a control for indicating the position of the actuating member to the control, and wherein the control operates to calculate and display a correct tool rotation speed.

17. The instrument of claim 7, wherein the input gear is operatively connected to a flexible drive member extending from the housing.

18. The instrument of claim 17 further comprising an electric motor coupled to the flexible drive member.

19. The instrument of claim 7, wherein the support structure includes a housing which contains the input gear, transition gear and output gear and further including a drive comprising an electric motor having an output shaft coupled with the input gear and a tool holding member coupled with the output gear and extending outside the housing.

20. A medical instrument for rotating a tool, the instrument comprising:
a housing;
an input gear mounted within the housing for rotation by a drive at a first speed;
an output gear mounted within the housing for rotation at a second speed and adapted to be coupled with the tool;
a planetary gear system mounted for operation between the input gear and the output gear, the planetary gear system including at least one fixed, internally toothed annulus gear and at least one externally toothed planet gear mounted for axial movement within the housing and for selective, meshing engagement with the internally toothed annulus gear; and
a movable actuating member coupled with the planet gear for moving the planet gear into and out of engagement with the internally toothed annulus gear and into and out of engagement with at least one of the input gear and the output gear to facilitate at least one of a step-up and a step-down in the second speed as compared to the first speed.

21. The instrument of claim 20 further comprising two of said fixed, internally toothed annulus gears, a first of the annulus gears being in line with the input gear and a second of the annulus gears being in line with the output gear, wherein the actuating member moves the planet gear axially between first and second positions with the first position being a meshing engagement with both the input gear and the first annulus gear and the second position being a meshing engagement with both the output gear and the second annulus gear.

22. The instrument of claim 21 further comprising a space formed between the first and second annulus gears defining a third position in which the planet gear is disengaged from both the first and second annulus gears.

23. The instrument of claim 22 further comprising an internally toothed carrier connected with the actuating member, wherein the planet gear is mounted for rotation on the carrier and an internally toothed portion of the carrier is selectively engageable with at least one of the input and output gears.

24. The instrument of claim 20 further comprising a plurality of planet gears rotatably mounted to a carrier, the carrier being connected with the actuating member for axial movement within the housing to selectively engage and disengage the planet gears and the annulus gear.

25. The instrument of claim 20 further comprising a handheld drive having a rotatable output connected with the input gear.

26. The instrument of claim 25, wherein the drive is a variable speed electric motor.

27. The instrument of claim 20, wherein the input gear is operatively connected with a flexible drive member extending from the housing.

28. The instrument of claim 27 further comprising an electric motor coupled with the flexible drive member.

29. The instrument of claim 20 further comprising a position indicating device coupled to the actuating member and electrically connected to a control for indicating the position of the actuating member to the control, wherein the control operates to calculate and display a correct tool rotation speed.

30. A handheld medical instrument for rotating a tool, the instrument comprising:

a support structure having a portion that may be gripped by a user;

a variable speed electric motor having an output rotatable at a first speed;

a tool rotating shaft extending from the support structure and adapted to be coupled to a tool and rotatable at a second variable speed; and a variable speed transmission operatively coupled between the output of the electric motor and the tool rotating shaft to transfer rotation therebetween, said transmission including a gear system which is selectively adjustable between at least two different ratios of the first speed relative to the second speed.

31. A handheld medical instrument for rotating a tool, the instrument comprising:

a support structure having a portion that may be gripped by a user;

an electric motor having an output rotatable at a first speed;

a tool rotating shaft extending from the support structure and adapted to be coupled to a tool and rotatable at a second variable speed;

a variable speed transmission operatively coupled between the output of the electric motor and the tool rotating shaft to transfer rotation therebetween, said transmission including a gear system which is selectively adjustable between at least two different ratios of the first speed relative to the second speed; and an actuating member exposed outside of the support structure and connected with the gear system to adjust the gear system between the different ratios.

32. A handheld medical instrument for rotating a tool, the instrument comprising:

a support structure having a portion that may be gripped by a user;

an electric motor having an output rotatable at a first speed;

a tool rotating shaft extending from the support structure and adapted to be coupled to a tool and rotatable at a second variable speed; and a variable speed transmission operatively coupled between the output of the electric motor and the tool rotating shaft to transfer rotation therebetween, said transmission including a planetary gear system which is selectively adjustable between at least two different ratios of the first speed relative to the second speed, said planetary gear system having an externally toothed planet gear adjustable between engaged and disengaged positions relative to an internally toothed annulus gear.

33. A handheld medical instrument for rotating a tool, the instrument comprising:

a support structure having a portion that may be gripped by a user;

an electric motor located outside of the support structure having an output rotatable at a first speed;

a tool rotating shaft extending from the support structure and adapted to be coupled to a tool and rotatable at a second variable speed;

a variable speed transmission operatively coupled between the output of the electric motor and the tool rotating shaft to transfer rotation therebetween, said transmission including a gear system which is selectively adjustable between at least two different ratios of the first speed relative to the second speed; and a flexible drive cable connecting the output of said motor to said variable speed transmission.

* * * * *